(12) United States Patent
Otsubo

(10) Patent No.: US 7,594,907 B2
(45) Date of Patent: Sep. 29, 2009

(54) DISPOSABLE PANTS-TYPE DIAPER HAVING BELT MEMBERS

(75) Inventor: Toshifumi Otsubo, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 3 days.

(21) Appl. No.: 11/924,129

(22) Filed: Oct. 25, 2007

(65) Prior Publication Data

US 2008/0114321 A1 May 15, 2008

(30) Foreign Application Priority Data

Nov. 15, 2006 (JP) ............................ 2006-309716

(51) Int. Cl.
*A61F 13/15* (2006.01)

(52) U.S. Cl. .................. 604/387; 604/385.03

(58) Field of Classification Search ............ 604/385.01, 604/385.201, 385.22, 385.24–385.3, 386–387
See application file for complete search history.

(56) References Cited

U.S. PATENT DOCUMENTS 3,688,767 A * 9/1972 Goldstein ................... 604/394
6,413,249 B1 * 7/2002 Turi et al. ................... 604/387
6,508,798 B1   1/2003 Widlund et al.
6,632,211 B2 * 10/2003 Otsubo .................. 604/385.22
6,648,868 B2 * 11/2003 Sayama et al. ......... 604/385.22
6,991,623 B2 * 1/2006 Tanaka et al. .......... 604/385.29
7,014,632 B2 * 3/2006 Takino et al. ............... 604/393
7,320,684 B2 * 1/2008 LaVon et al. ................ 604/392
2002/0173764 A1 * 11/2002 Takino et al. .......... 604/385.28

FOREIGN PATENT DOCUMENTS

JP        09-510385 A     10/1997

* cited by examiner

*Primary Examiner*—Michele Kidwell
(74) *Attorney, Agent, or Firm*—Lowe Hauptman Ham & Berner, LLP

(57) ABSTRACT

A pants-type diaper includes a crotch region which is provided on the inner surface in a zone put aside toward a front waist region and in a zone put aside toward a rear waist region with belt-like members, respectively, both extending across a body fluid absorbent structure. Each of the belt-like members has distal ends bonded to leakage barrier means formed along side edges of the body fluid absorbent structure. Intermediate segment extending between the distal ends is free from the inner surface of the crotch region. The belt-like members are integrated with each other only along respective middle segments thereof as viewed in a transverse direction.

16 Claims, 10 Drawing Sheets

DISPOSABLE PANTS-TYPE DIAPER HAVING BELT MEMBERS

RELATED APPLICATIONS

The present application is based on, and claims priority from, Japan Application Number 2006-309716,filed Nov. 15, 2006, the disclosure of which is hereby incorporated by reference herein in its entirety.

BACKGROUND OF THE INVENTION

The present invention relates to a disposable pants-type diaper and more particularly to such a pants-type diaper facilitating side edges of a crotch region to be held in close contact about the wearer's legs.

There are conventionally well known disposable diapers including elastic members arranged in a stretched state to the side edges of the crotch region in the diaper so as to extend about the wearer's legs. Upon contraction, these elastic members function to put the side edges of the crotch region in close contact about the respective legs and thereby to prevent bodily fluids from leaking beyond leg-openings.

For example, National Publication of Translated Version No. 1997-510385 (REFERENCE) discloses an open-type diaper wherein a liquid-pervious inner casing sheet covering an absorbent structure is provided on the side of its inner surface with a pair of flaps. These flaps are symmetrically laid about a longitudinal center line of the diaper and bonded to the inner casing sheet along the side edges of the diaper. Sections of the flaps transversely extending toward the longitudinal center line are connected with each other in the crotch region. These flaps are spaced from each other in front and behind the crotch region to define an opening adapted for passage of urine and an opening adapted for passage of feces. These flaps respectively include elastic strings extending in a back-and-forth direction along peripheral edges of the respective openings and attached in a stretched state to the respective flaps. Upon the contraction of the elastic strings, the diaper is deformed in the back-and-forth direction as well as in the transverse direction. Deformation in the transverse direction biases the side edges of the diaper to come in close contact about the wearer's legs and thereby serves to prevent possible leakage of bodily fluids about the wearer's legs.

With the conventional diapers as have been described above, if urine and/or feces flows on the flaps instead of flowing through the associated openings and being absorbed by the absorbent structure as expected, such body waste would miss out on a chance to come in contact with the absorbent structure, resulting in problems that the wearer's skin would be soiled with body waste and/or leakage of body waste would occur about the wearer's legs.

SUMMARY OF THE INVENTION

In view of the problem as has been described above, it is an object of the present invention to provide a pants-type diaper facilitating side edges of the diaper's crotch region to be reliably held in close contact around the wearer's legs. It is another object of the present invention to provide such a diaper with means adapted to prevent a possible leakage from occurring about the wearer's legs.

There is provided a disposable pants-type diaper having a crotch region, a front waist region extending forward from the crotch region and a rear waist region extending rearward from the crotch region, wherein the front waist region and the rear waist region are bonded to each other along respective pairs of side edges thereof to form a pants-type skin coverable chassis, the crotch region is provided in its middle zone as viewed in a transverse direction with a body fluid absorbent structure formed from an assembly of body fluid absorbent materials and the body fluid absorbent structure is provided along its side edges with leakage barrier means respectively formed from a sheet material and including elastic members stretched in a back-and-forth direction of the crotch region and attached in such a stretched state to the respective side edges.

The present invention further comprises the following: In the pants-type diaper folded back so that the front and rear waist regions have respective inner surfaces put flat together, the crotch region is provided on an inner surface thereof in a zone put aside toward a front waist region and in a zone put aside toward a rear waist region as viewed from a bottom of the crotch region with a pair of front and rear belt-like members, respectively, both extending in the transverse direction across a body fluid absorbent structure and bonded at distal ends to the leakage barrier means so that respective intermediate segments of the belt-like members extending between the distal ends are free from an inner surface of the body fluid absorbent structure and the belt-like members are integrated with each other only along respective middle segments thereof, leaving the belt-like members free from each other between the middle segments and the distal ends.

According to one preferred embodiment of the invention, a pair of the belt-like members have respectively the distal ends lying at the same distance from a transverse center line bisecting a dimension of the pants-type diaper as measured along the inner surface.

According to another preferred embodiment of the invention, the belt-like members are elastically stretchable and contractible and attached to the diaper while the belt-like members are stretched in the transverse direction.

According to still another preferred embodiment of the invention, the respective side edges of the front waist region and the rear waist region are adapted to be bonded together immediately prior to wearing just before and to be separated from and reconnected to each other after the diaper has been put on the wearer's body.

According to yet another preferred embodiment of the invention, the leakage barrier means comprises a pair of flaps extending from the side edges of the body fluid absorbent structure in the transverse direction.

According to further another preferred embodiment of the invention, the leakage barrier means comprises a pair of leakage barrier cuffs respectively formed along the side edges of the body fluid absorbent structure so as to be able to stand up from the inner surface.

In the case of the disposable pants-type diaper according to the present invention, starting from the state in which the front and rear waist regions have respective inner surfaces put flat together, the front and rear waist regions may be flared so as to broaden the waist-opening in a circle. Simultaneously, the paired front and rear belt-like members having thitherto extended linearly in the transverse direction are deformed and spaced from the inner surface of the diaper so as to describe two V-shapes opening forward and rearward from the bottoms defined by the integrated middle segments of the belt-like members. In response to such deformation, the leakage barrier formed along the side edges of the body fluid absorbent structure stand up in close contact about the wearer's legs. These leakage barrier means standing up in this manner reliably prevent possible leak of body fluids from occurring about the wearer's legs. The front opening defined by the V-shape described by the front belt-like member serves to guide urine while the rear opening defined by the V-shape described by the rear belt-like member serves to guide feces. The front and rear belt-like members are spaced from each other between the middle segments and the distal ends to define the voids adapted to receive an amount of body waste which passes neither through the front opening nor through the rear opening and to guide downward such amount of body waste toward the body fluid absorbent structure.

According to the embodiment of the present invention wherein the belt-like members are stretchable and contractible and attached in a stretched state to the diaper, a contractile force of these belt-like members facilitates the leakage barrier means to stand up. Furthermore, these belt-like members are stretched and contracted as these belt-like members come in contact with the wearer's body without interference with movement of the wearer's body.

Other embodiments of the invention and effects provided thereby will be described later.

DETAILED DESCRIPTION OF THE PREFERRED EMBODIMENTS

Details of a disposable pants-type diaper according to the present invention will be more fully understood from the description given hereunder with reference to the accompanying drawings.

Figure 1:
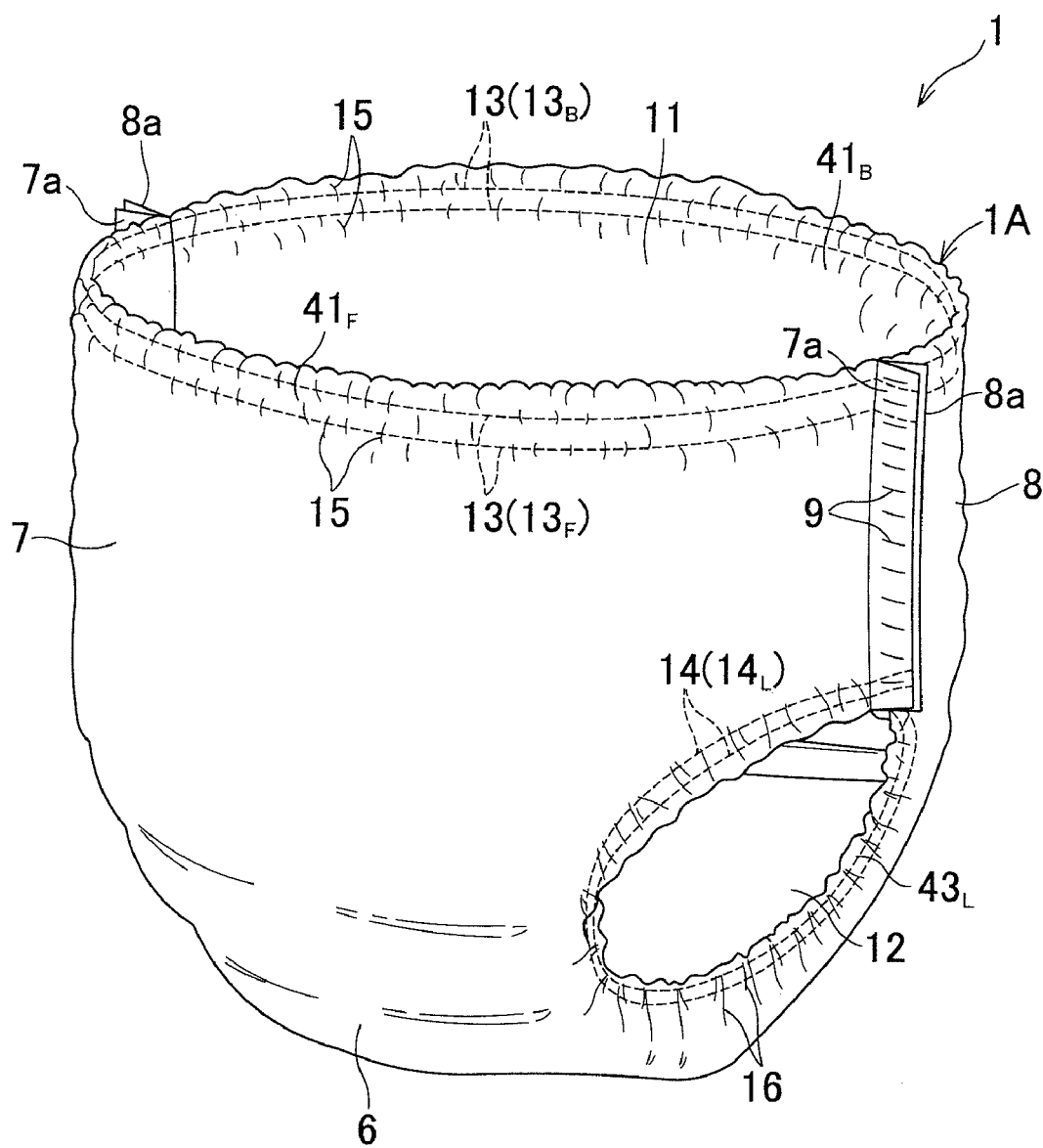
FIG. 1 is a perspective view showing a pants-type diaper.

FIG. 1 is a perspective view showing a disposable pants-type diaper 1 as put on the wearer's body wherein transverse, back-and-forth and vertical directions are indicated by arrows X, Y and Z, respectively. The pants-type diaper 1 has a crotch region 6, a front waist region 7 extending forward from the crotch region 6 and a rear waist region 8 extending rearward from the crotch region 6 which cooperate together to form a skin coverable chassis 1A. The front and rear waist regions 7, 8 respectively have a pair of lateral edges 7a, 7a and a pair of lateral edges 8a, 8a. The respective lateral edges 7a, 7a of the front waist region 7 are bonded to the respective lateral edges 8a, 8a of the rear wait region 8 at spots 9 arranged intermittently in the vertical direction so as to form a waist-opening 11 and simultaneously cooperate with the crotch region 6 to form a pair of leg-openings 12. A peripheral edge of the waist-opening 11 is defined by a front waist region flap $41_F$ and a rear waist region flap $41_B$ and provided with a waist elastic member 13. More specifically, elastic members $13_F$, $13_R$ are bonded in a stretched state to the respective flaps $41_F$, $41_B$. Peripheral edges of the leg-openings 12 are defined by a right leg flap $43_R$ (See FIG. 3) and a left leg flap $43_L$ and provided with leg elastic members 14. More specifically, a right leg elastic member $14_R$ (See FIG. 3) and a left leg elastic member $14_L$ are bonded in a stretched state to the respective leg flaps $43_R$ and $43_L$.

Figure 2:
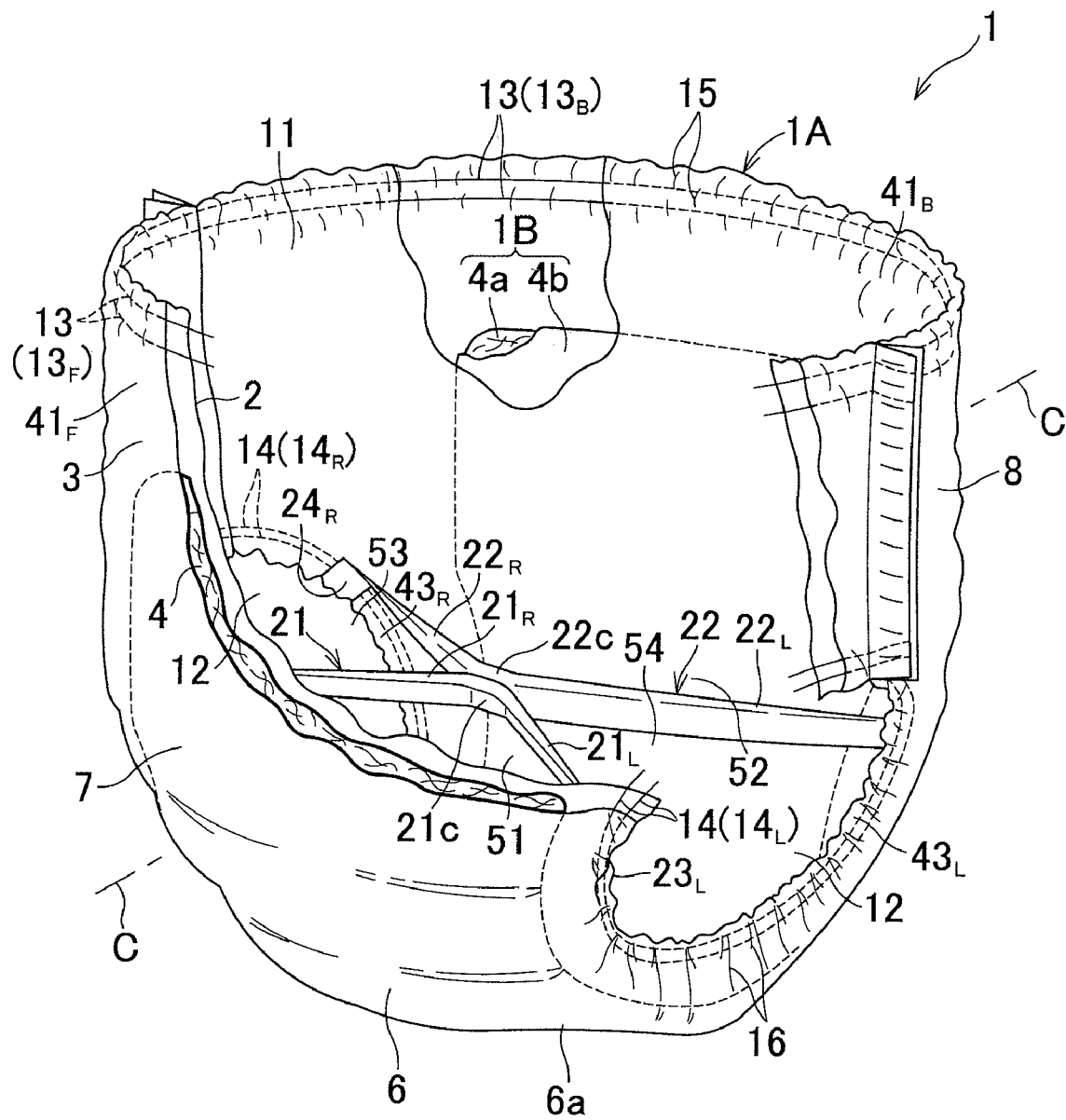
FIG. 2 is a partially cutaway perspective view showing the pants-type diaper.

FIG. 2 is a perspective partially cutaway view showing the pants-type diaper of FIG. 1. The pants-type diaper 1 comprises the skin coverable chassis 1A having its inner side formed of a liquid-pervious bodyside liner 2 and its outer side formed of a liquid-impervious outer sheet 3, and a body fluid absorbent structure 1B interposed between these two sheets 2, 3. The front and rear waist region elastic members $13_F$, $13_B$ as well as the leg right and left elastic members $14_R$, $14_L$ are interposed between the bodyside liner 2 and the outer sheet 3 and bonded at least one of these elements 2, 3 by means of hot melt adhesives (not shown). It will be appreciated in FIGS. 1 and 2 that the front and rear waist flaps $41_F$, $41_B$ as well as the leg right and left flaps $43_R$, $43_L$ are formed with gathers 15, 16, respectively, under contraction of these elastic members $13_F$, $13_B$, $14_R$, $14_L$.

The pants-type diaper 1 includes, in addition to the skin coverable chassis 1A, belt-like front and rear cross members 21, 22 extending across the body fluid absorbent structure 1B between the right leg flap $43_R$ and the left leg flap $43_L$. These front and rear cross members 21, 22 respectively have middle segments 21c, 22c extending on a back-and-forth center line C-C so as to bisect a dimension of the pants-type diaper 1 in the transverse direction X and, along these middle segments 21c, 22c, these front and rear cross members 21, 22 are bonded to each other by use of bonding means (not shown) such as appropriate adhesives, sealing treatments or pressure-sensitive adhesive double coated tapes. The front cross member 21 defines a V-shape opening forward with its middle segment 21c as a bottom of this V-shape. The halves $21_R$, $21_L$ of this front cross member 21 respectively have distal ends $23_R$, $23_L$ bonded to respective inner surfaces of the leg right and left flaps $43_R$, $43_L$ (See FIG. 3). In the similar manner, the rear cross member 22 defines a V-shape opening rearward with its middle segment 22c as a bottom of this V-shape. The halves $22_R$, $22_L$ of this rear cross member 22 respectively have distal ends $24_R$, $24_L$ bonded to respective inner surfaces of the leg right and left flaps $43_R$, $43_L$ (See FIG. 3). The leg right and left flaps $43_R$, $43_L$ are normally drawn inwardly of the pants-type diaper 1 by the presence of these front and rear cross members 21, 22.

The body fluid absorbent structure 1B is an assembly of body fluid absorbent materials located in a middle zone of the pants-type diaper 1 as viewed in the transverse direction X and comprising a plurality of body fluid absorbent particles 4a such as fluff pulp and/or super-absorbent polymer particles wrapped with a sheet material 4b such as tissue paper or nonwoven fabrics characterized by high liquid-permeability and, more preferably, by high liquid-permeability as well as by high liquid-spreadability.

Figure 3:
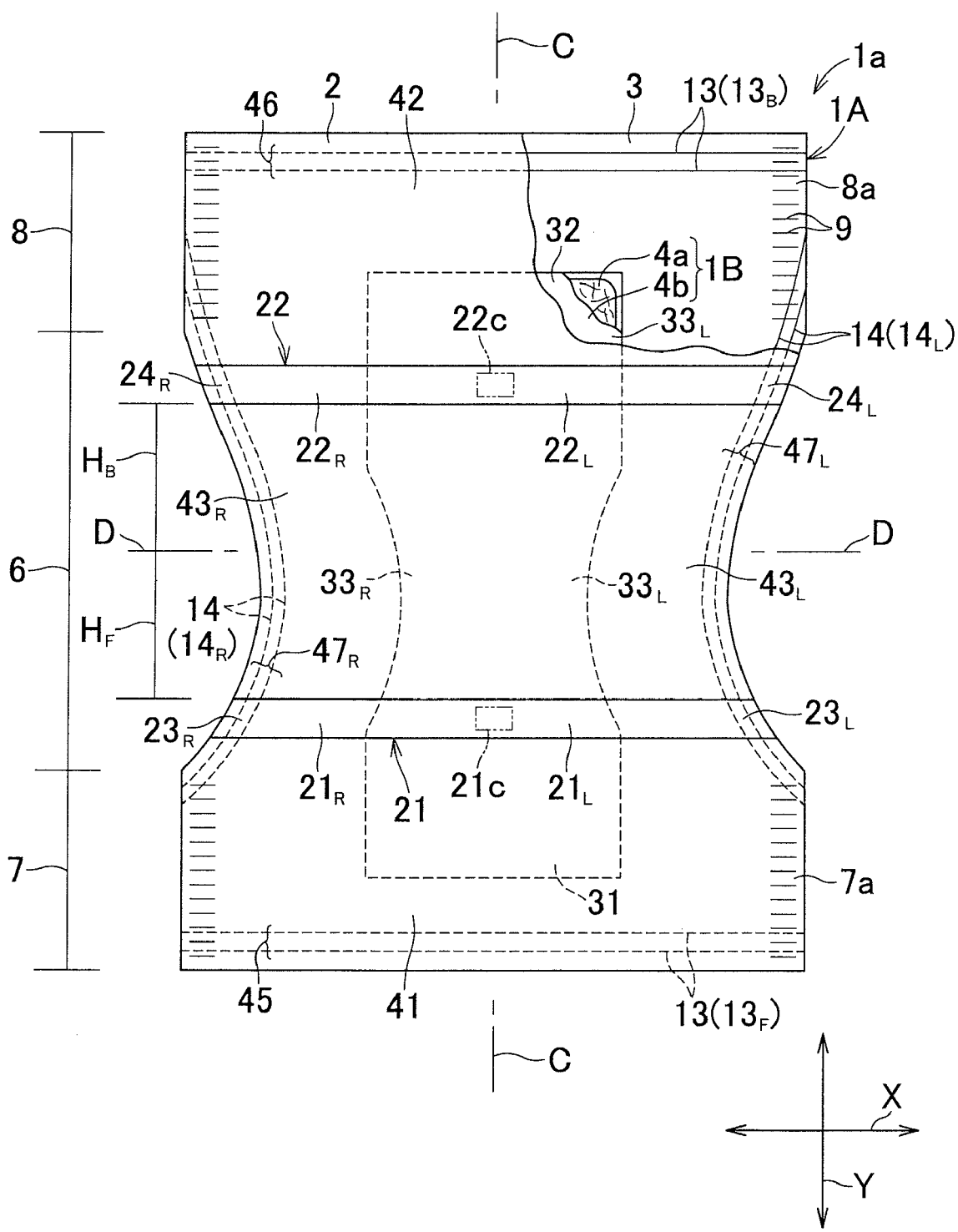
FIG. 3 is a plan view showing the pants-type diaper of FIG. 1 as has been developed.

FIG. 3 is a partially cutaway plan view of the pants type diaper 1 of FIGS. 1 and 2 obtained by peeling the front and rear waist regions 7, 8 off from each other at the spots 9, peeling the front and rear cross members 21, 22 off from each other along the respective middle segments 21c, 22c thereof and finally developing the crotch region 6, the front waist region 7 and rear waist regions 8 in the transverse direction X and the back-and-forth direction Y. As will be seen in FIG. 3, the hourglass-like shaped body fluid absorbent structure 1B laid in a middle zone of the chassis 1A as viewed in the transverse direction X has front and rear ends 31, 32 both extending in the transverse direction, and right and left side edges $33_R$, $33_L$ both extending in the back-and-forth direction Y. The bodyside liner 2 and the outer sheet 3 are the same in shape as well as in size and extend outward beyond the front and rear ends 31, 32 and the left and right side edges $33_L$, $33_R$. The bodyside liner 2 and the outer sheet 3 are put flat and bonded together over respective sections extending outward beyond the front and rear ends 31, 32 and the left and right side edges $33_L$, $33_R$ by use of appropriate adhesives or sealing treatments so as to form the front waist flap $41_F$, the rear waist flap $41_B$, the right leg flap $43_R$ and the left leg flap $43_L$. In the front and rear waist flaps $41_F$, $41_B$, the waist front and rear elastic members $13_F$, $13_B$ cooperate with sections of the bodyside liner 2 and the outer sheet 3 extending in vicinities of these elastic members $13_F$, $13_B$ to define waist front and rear elastic zones 45, 46 adapted to generate gathers 15 (See FIG. 1) as the waist front and rear elastic members $13_F$, $13_B$ contract. In the leg right and left flaps $43_R$, $43_L$, the leg right and left elastic members $14_R$, $14_L$ cooperate with sections of the bodyside liner 2 and the outer sheet 3 extending in vicinities of these elastic members $14_R$, $14_L$ to define leg right and left elastic zones $47_R$, $47_L$ adapted to generate gathers 16 (See FIG. 1) as these elastic members $14_R$, $14_L$ contract. The body fluid absorbent structure 1B interposed between the bodyside liner 2 and the outer sheet 3 is bonded to at least one of these elements 2, 3 by use of appropriate adhesives or sealing treatments.

Referring to FIG. 3, of the front cross member 21 the distal ends $23_R$, $23_L$ are bonded to the respective inner surfaces of the leg right and left elastic zones $47_R$, $47_L$ using appropriate adhesives or sealing treatments but an intermediate segment between the two distal ends $23_R$, $23_L$ is free from the bodyside liner 2, i.e., this intermediate segment can be freely spaced from the bodyside liner 2. In the similar manner, of the rear cross member 22, the distal ends $24_R$, $24_L$ are bonded to the respective inner surfaces of the leg right and left elastic zones $47_R$, $47_L$ using appropriate adhesives or sealing treatments but an intermediate segment between the two distal ends $24_R$, $24_L$ is free from the bodyside liner 2, i.e., this intermediate segment can be free spaced from the bodyside liner 2. Each of these front and rear cross members 21, 22 has a dimension in the back-and-forth direction Y preferably in a range of 5 to 20 mm. A distance $H_F$ measured along the inner surface of the skin coverable chassis 1A from a transverse center line D-D to the distal ends $23_R$, $23_L$ of the front cross member 21 is equal to a distance $H_B$ measured in the same manner from the transverse center line D-D to the distal ends $24_R$, $24_L$ of the rear cross member 22. Accordingly, these two cross members 21, 22 extend to near-horizontal at levels which are symmetrical about the transverse center line D-D as seen in FIG. 2. In the case of the pants-type diaper 1 for baby, the distance $H_F$, $H_B$ is preferably in a range of 20 to 150 mm, more preferably in a range of 40 to 80 mm.

The pants-type diaper 1a in such a state as shown in FIG. 3 is folded back on itself along the transverse center line D-D bisecting the dimension of the diaper 1a in the back-to-forth direction with the bodyside liner 2 inside. Simultaneously, the respective middle segments 21c, 22c of the front and rear cross members 21, 22 are bonded to each other and the front and rear waist regions 7, 8 are bonded to each other along the respective side edges 7a, 7a; 8a, 8a. In this manner, the pants-type diaper 1 folded back and flattened is obtained. When the waist-opening 11 and the leg-openings 12 are broadened substantially in circles in order to put the diaper 1 on the wearer's body as seen in FIGS. 1 and 2, the crotch region 6 as well as the front and rear waist regions 7, 8 are deformed so as to become convex outward. Consequently, the crotch region 6, the front waist region 7 and the rear waist region 8 have transverse dimensions thereof are apparently reduced with respect to those in FIG. 3 and thereupon the front and rear cross members 21, 22 are deformed so as to describe V-shapes, respectively. Such deformation of the cross members 21, 22 generates a front void 51 between the front cross member 21 and the bodyside liner 2, a rear void 52 between the rear cross member 22 and the bodyside liner 2 (See FIG. 2), a right void 53 between the respective right halves $21_R$, $22_R$ of the front and rear cross members 21, 22, and a left void 54 between the respective left halves $21_L$, $22_L$ of the front and rear cross members 21, 22 (See FIG. 2). The pants-type diaper 1 may be put on the wearer's body with the right leg guided through the right void 53 and the left leg guided through the left void 54. With the pants-type diaper 1 put on the wearer's body in this manner, the respective middle segments 21c, 22c of the front and rear cross members 21, 22 will be located between the external genital and the anus so that urine will be discharged toward the front void 51 and feces will be discharged toward the rear void 52.

The front and rear cross members 21, 22 are adapted to contract in the transverse direction X as the pants-type diaper 1 flatly folded back on itself is unfolded to its three-dimensional state as seen in FIG. 2. In this state, the respective right halves $21_R$, $22_R$ cooperate with each other to draw the right leg elastic zone $47_R$ toward the back-and-forth center line C-C of the pants-type diaper 1 so as to facilitate the right leg flap $43_R$ to stand up in the vertical direction Z of the pants-type diaper 1 on a proximal end defined by a vicinity of the right side edge $33_R$ of the body fluid absorbent structure 1B (See FIG. 2). Contraction of the right leg elastic member $14_R$ in the right leg flap $43_R$ also facilitates this flap $43_R$ to stand up. In this way, the right leg flap $43_R$ stands up along the right side edge $33_R$ of the body fluid absorbent structure 1B and serves as leakage barrier means against sideway leak of body fluid which otherwise might occur. In other words, the right leg flap $43_R$ functions as a leakage barrier. Particularly, a portion of the right leg flap $43_R$ rising along the bottom 6a of the crotch region 6 (See FIG. 2) is kept in close contact with a vicinity of the wearer's inguinal region and effectively prevents possible leakage of body fluids from occurring along the wearer's skin. This effect is true also with respect to the respective left halves $21_L$, $22_L$ of the front and rear cross members 21, 22. Specifically, these left halves $21_L$, $22_L$ are tightened and the left leg elastic member $14_L$ contract as the waist-opening 11 is broadened. Thereupon the left leg flap $43_L$ stands up along the left side edge $33_L$ of the body fluid absorbent structure 1B so as to form in a vicinity of the bottom 6a of the crotch region 6 a leakage barrier which is also reliably put in close contact with a vicinity of the wearer's inguinal region.

In such pants-type diaper 1, the front and rear cross members 21, 22 may be formed from stock materials selected from the group consisting of non-stretchable nonwoven fabrics, woven fabrics, plastic films and rubber sheets. It is also possible to use sheet strips such as nonwoven fabrics, plastic films or rubber sheets each elastically stretchable in the transverse direction X to form the front and rear cross members 21, 22. Such elastically stretchable sheet strips may be attached in a stretched state to the pants-type diaper 1 to ensure that the leg right and left flaps $43_R$, $43_L$ further easily stand up as the pants-type diaper 1 is put on the wearer's body. As stock materials for the bodyside liner 2, body fluid pervious nonwoven fabrics or perforated plastic films may be used and, as stock materials for the outer sheet 3, sheet materials such as body fluid impervious plastic films or nonwoven fabrics may be used. With respect to the front and rear cross members 21, 22, as an variant of the embodiment shown in FIG. 3, the distances $H_F$, $H_B$ from the transverse center line D-D may be differentiated, for example, the distance $H_B$ may be set to be larger than the distance $H_F$ to improve a fit of the pants-type diaper 1 to the wearer's body.

Figure 4:
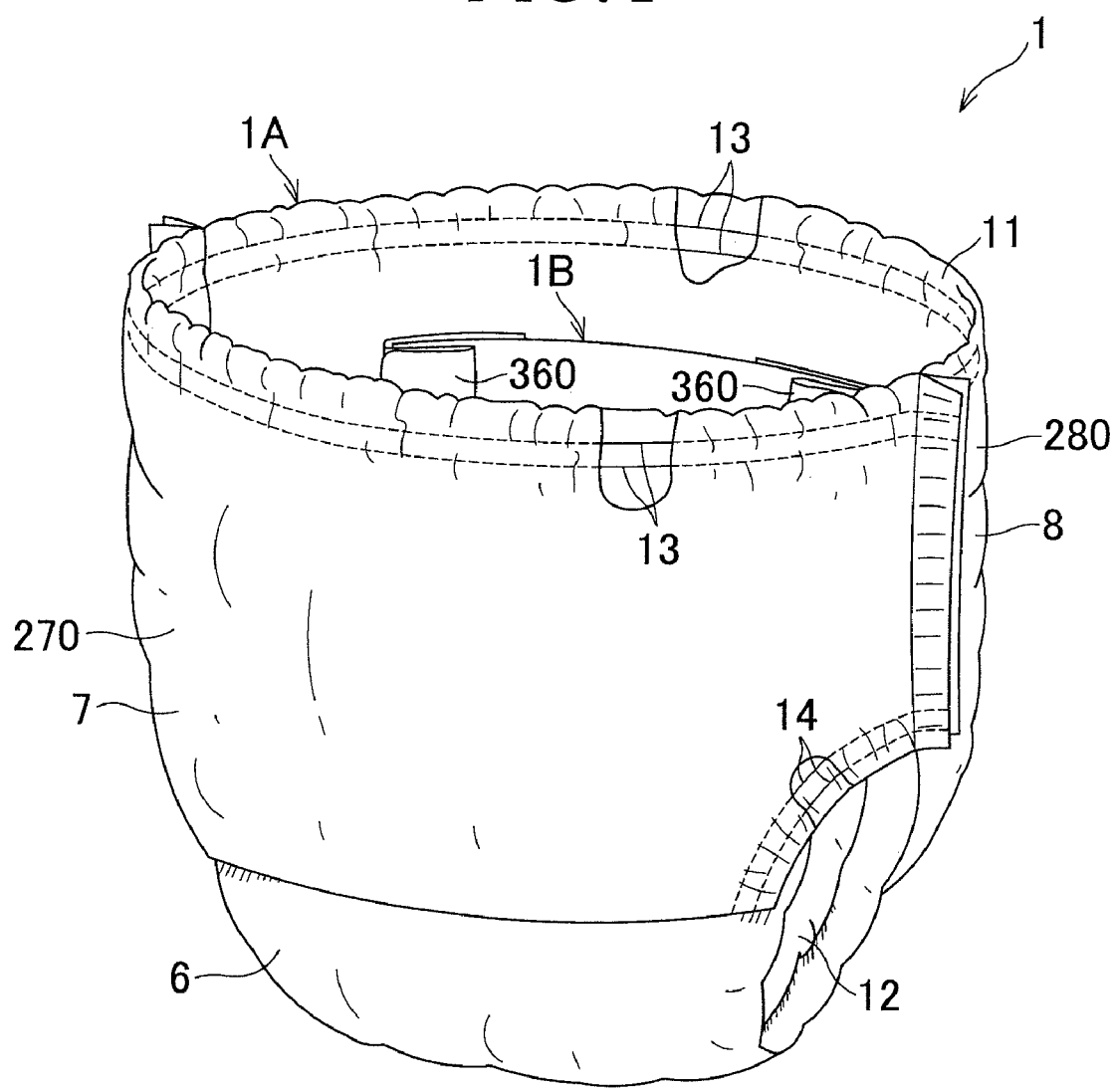
FIG. 4 is a view similar to FIG. 1, showing one preferred embodiment of the invention.
Figure 4:
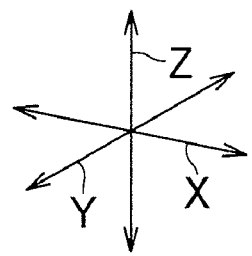

FIG. 4 is a partially cutaway perspective view showing the pants-type diaper 1 according to one preferred embodiment of the invention wherein components respectively having functions similar to those of the pants-type diaper 1 shown in FIG. 1 are respectively designated by similar reference numerals. The pants-type diaper 1 shown in FIG. 4 basically comprises the pants-shaped skin coverable chassis 1A and the body fluid absorbent structure 1B attached to the inner surface of the chassis 1A. A plurality of waist elastic members 13 are attached in a stretched state to the periphery extending along the waist-opening 11 of the skin coverable chassis 1A. With respect to the leg-openings 12, a plurality of leg elastic members 14 are attached in a stretched state to front and rear sheets 270, 280 forming the front and rear waist regions 7, 8 inclusive of peripheral edges extending around approximately upper halves of the respective leg-openings 12 so that these elastic members 13 describe semicircles. The body fluid absorbent structure 1B is laid on the inner surface of the skin coverable chassis 1A.

Figure 5:
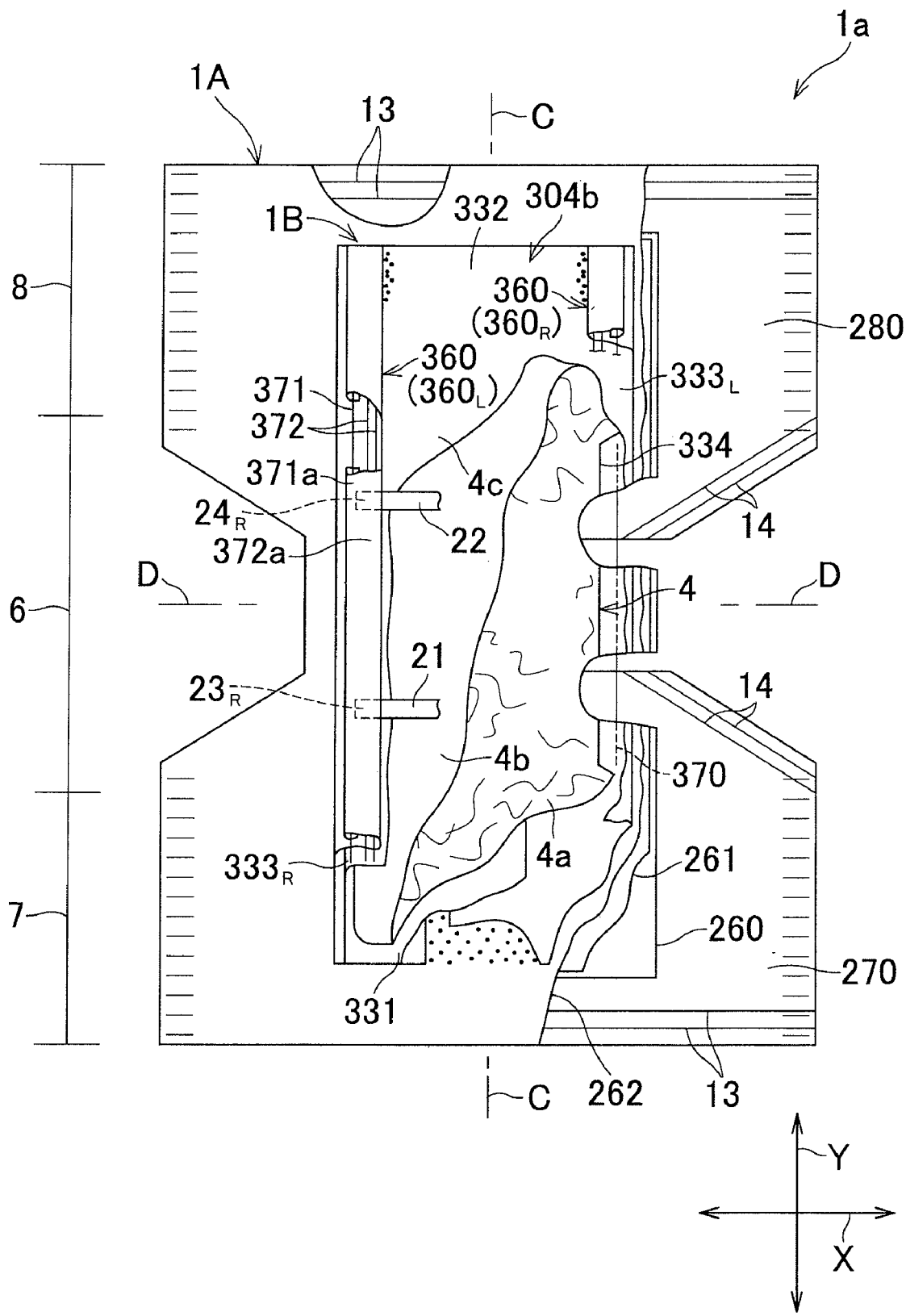
FIG. 5 is a view similar to FIG. 3, showing the pants-type diaper of FIG. 4.
Figure 6:
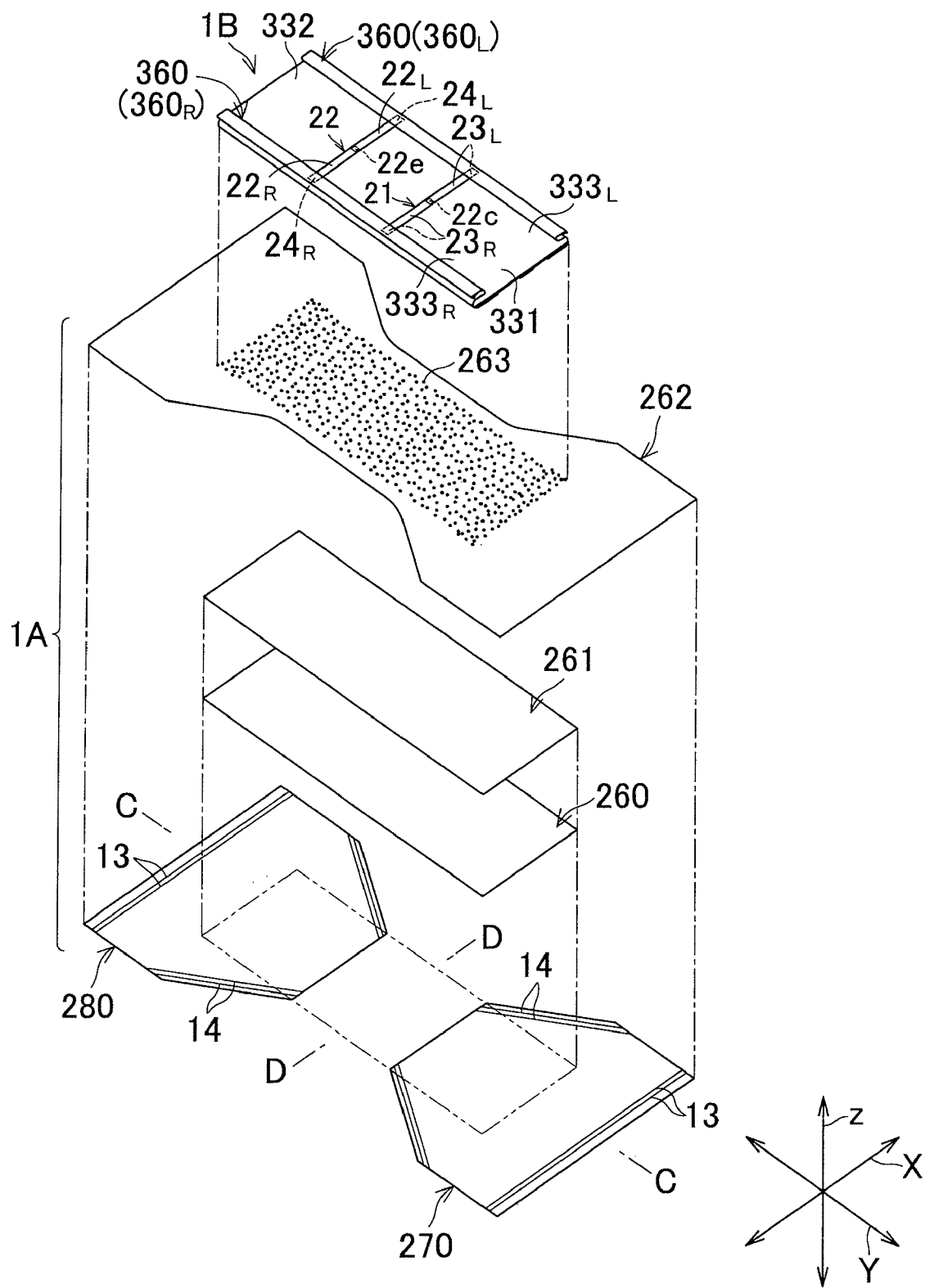
FIG. 6 is an exploded perspective view showing the pants-type diaper of FIG. 4.

FIG. 5 is a partially cutaway plan view of the pants type diaper 1a obtained by peeling the front and rear waist regions 7, 8 off from each other at the spots 9 and finally developing the crotch region 6, the front waist region 7 and rear waist regions 8 in the transverse direction X and the back-and-forth direction Y and FIG. 6 is an exploded perspective view of this pants-type diaper 1a of FIG. 5. With respect to this developed pants-type diaper 1a, FIG. 5 indicates also the transverse center line D-D which is orthogonal to the back-and-forth center line C-C and bisects the vertical dimension of the diaper 1a.

The skin coverable chassis 1A comprises the hexagonal front sheet 270 defining the front waist region 7 and a part of the crotch region 6, the hexagonal rear sheet 280 defining the rear waist region 8 and a part of the crotch region 6 and a center sheet 260 defining a part of the crotch region 6. These front and rear sheets 270, 280 are provided on the respective inner surfaces thereof with the waist elastic members 13 and the leg elastic members 14. Front and rear ends of the center sheet 260 are bonded to the respective inner surfaces (i.e., upper surfaces as viewed in FIG. 6) of the front and rear sheets 270, 280, respectively, by means of hot melt adhesives (not shown) so as to connect the front and rear sheets 270, 280 to each other. An intermediate sheet 261 formed of rectangular water-impervious plastic film serving as the liquid-impervious outer sheet is placed on the inner surface of the center sheet 260 and an hourglass-shaped inner sheet 262 is placed on the inner surface of the intermediate sheet 261. The intermediate sheet 261 has a shape nearly the same as the center sheet 260 but has a size slightly smaller than the center sheet 260. In shape as well as in size, the inner sheet 262 is substantially the same as a combination of the front sheet 270, the rear sheet 280 and the center sheet 260 in the hourglass-shaped assembly. These elements 270, 280, 260, 261 and 262 are intermittently bonded together in respective overlap regions. The body fluid absorbent structure 1B is bonded to the inner surface of the inner sheet 262. More specifically, the inner sheet 262 is intermittently coated with hot melt adhesive 263 and substantially entire outer surface of the body fluid absorbent structure 1B is intermittently bonded to the inner sheet 262 by means of said hot melt adhesive 263.

As will be apparent from FIG. 5, the body fluid absorbent structure 1B presents a rectangle which is relatively long in the back-and-forth direction Y and contoured by a pair of side edges $333_R$, $333_L$ extending in parallel to the back-and-forth center line C-C, front and rear ends 331, 332 extending in the transverse direction X of the pants-type diaper 1 orthogonally to the side edges $333_R$, $333_L$, and leakage barrier cuffs 360 made of a nonwoven fabric formed along the respective side edges $333_R$, $333_L$. Such body fluid absorbent structure 1B is an assembly of body fluid absorbent materials comprising fluff pulp, body fluid absorbent particles 4a, tissue paper 4b wrapping a mixture of fluff pulp and body fluid absorbent particles 4a, and body fluid pervious skin-contactable sheet 4c placed upon the tissue paper 4b (See FIG. 8). The particles 4a are distributed on the tissue paper 4b so as to present the hourglass-like shape having a transverse dimension which is smaller in the crotch region 6 than in the front and rear waist regions 7, 8, i.e., provided along the side edges of the crotch region 6 with concave cutouts 334. The skin-contactable sheet 4c extends laterally beyond the edges of the concave cutouts 334 in the crotch region 6 and, outside these edges, the skin-contactable sheet 4c is placed on itself, preferably bonded to itself by means of hot melt adhesives (not shown).

The body fluid absorbent structure 1B further includes the front and rear cross members 21, 22. The distal ends $23_R$, $23_L$ of the front cross member 21 are bonded to the leakage barrier cuffs 360, more specifically, to right and left leakage barrier cuffs $360_R$, $360_L$ which are symmetric about the back-and-forth center line C-C by use of appropriate adhesives or sealing treatments. The distal ends $24_R$, $24_L$ of the rear cross member 22 also are bonded to the respective leakage barrier cuffs 360 (See FIG. 9). The diaper 1a is folded back onto itself along the transverse center line D-D, the front and rear waist regions are bonded together at the spots 9 and thereby the diaper 1a is shaped into the pants-type diaper 1. Simultaneously, the front and rear cross members 21, 22 are bonded to each other along the respective middle segments 21c, 22c thereof by use of appropriate adhesives or sealing treatments. With the pants-type diaper 1 obtained in this manner, the right half $21_R$ and the left half $21_L$ of the front cross member 21 are deformed so as to describe a V-shape while the right half $22_R$ and the left half $22_L$ of the rear cross member 22 are deformed so as to describe a V-shape in response to the waist-opening 11 being broadened as seen in FIG. 4 and thereby the crotch region 6, the front waist region 7 and the rear waist region 8 being made convex outward. The front and rear cross members 21, 22 deformed in this manner draw the respective leakage barrier cuffs 360 toward the back-and-forth center line C-C and thereby facilitate the respective leakage barrier cuffs 360 to stand up from the side edges $333_R$, $333_L$ of the body fluid absorbent structure 1B (See FIG. 9).

Figure 7:
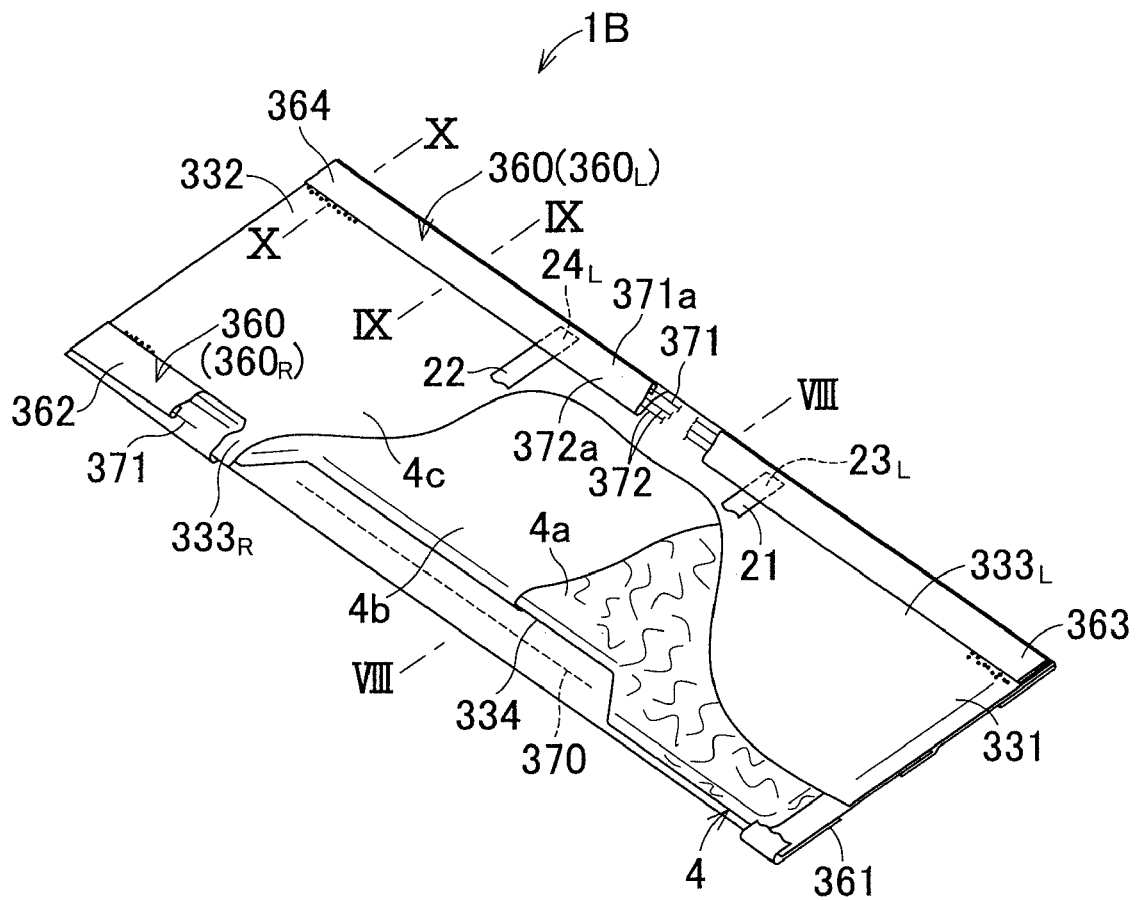
FIG. 7 is a partially cutaway perspective view showing a body fluid absorbent structure.
Figure 7:
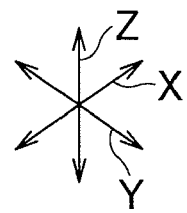
Figure 8:
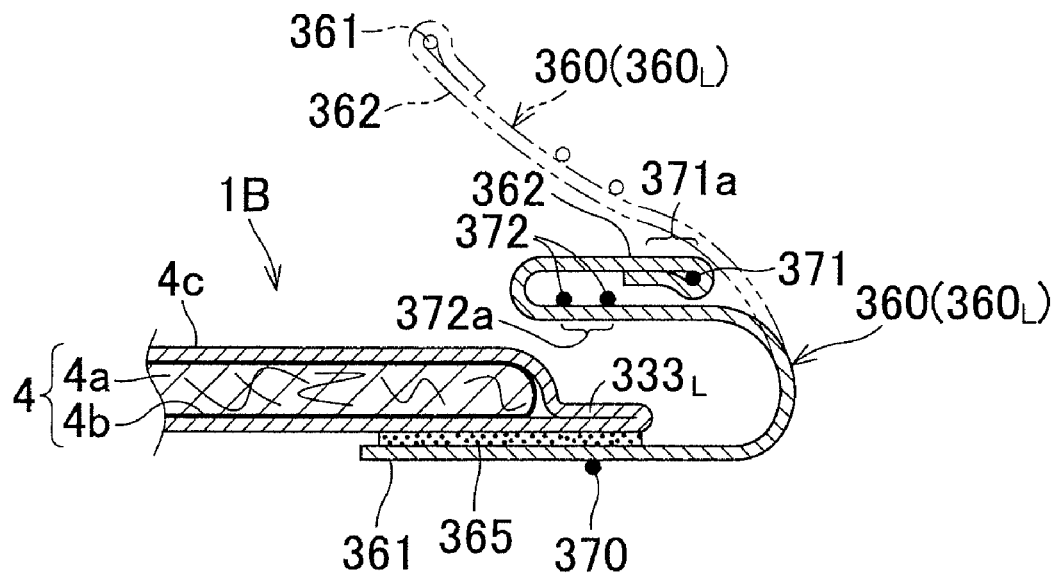
FIG. 8 is a sectional view taken along the line VIII-VIII in FIG. 7.
Figure 9:
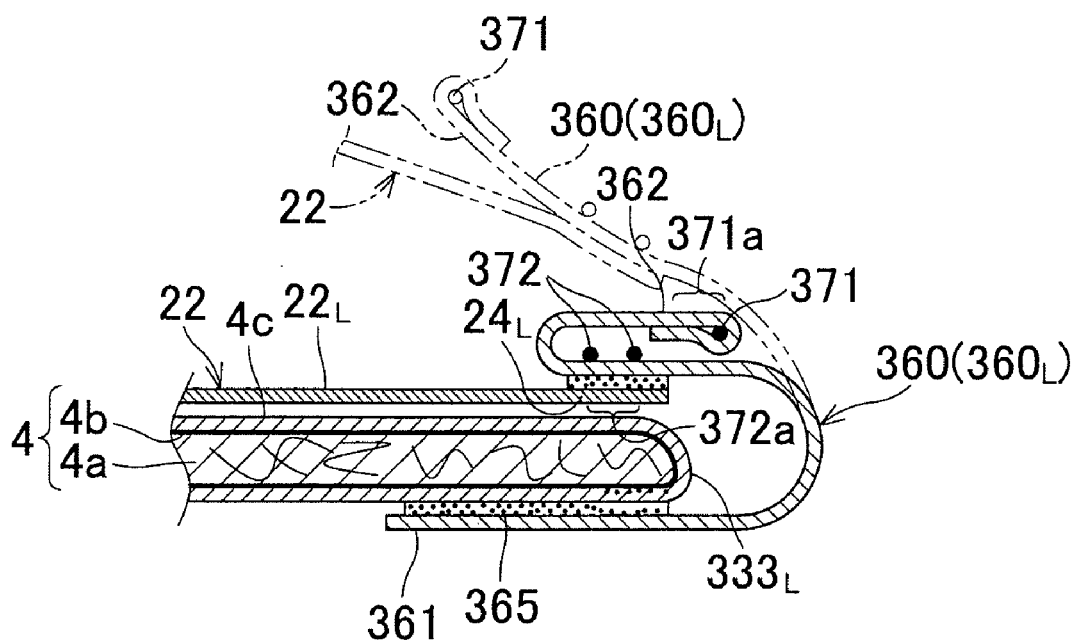
FIG. 9 is a sectional view taken along the line IX-IX in FIG. 7.
Figure 10:
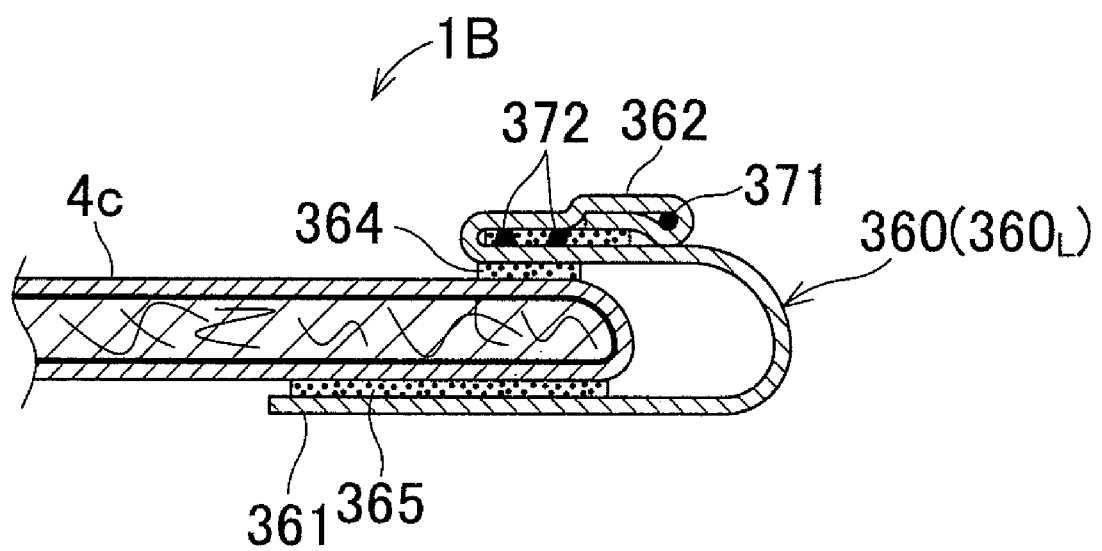
FIG. 10 is a sectional view taken along the line X-X in FIG. 7.

FIG. 7 is a partially cutaway perspective view showing the body fluid absorbent structure 1B, FIG. 8 is a sectional view taken along the line VIII-VIII in FIG. 7, FIG. 9 is a sectional view taken along the line IX-IX in FIG. 7 and FIG. 10 is a sectional view taken along the line X-X in FIG. 7. Each of the leakage barrier cuffs 360 is formed of suitable sheet materials and extends along the associated side edge $333_R$ or $333_L$ of the body fluid absorbent structure 1B. As the sheet materials, hydrophobic, preferably, not only hydrophobic but also liquid-impervious, more preferably, hydrophobic, air-permeable and liquid-impervious nonwoven fabrics or plastic films may be used. Each of the leakage barrier cuffs 360 is folded back in a Z-shape or an inverted Z-shape as viewed in the transverse direction X of the body fluid absorbent structure 1B and comprises an outer edge 361 extending on the side defined by the outer surface of the body fluid absorbent structure 1B and an inner edge 362 extending on the side defined by the inner surface of the body fluid absorbent structure 1B wherein the outer edge 361 is fixed to the skin-contactable sheet 4c by means of adhesive 365. The outer edge 361 is provided along a zone corresponding to the concave cutout 334 of the body fluid absorbent structure 1B with single or plural elastic members 370 for the crotch region 6 bonded in a stretched or non-stretched state to the outer edge 361 by means of hot melt adhesives (not shown). Referring to FIGS. 8 and 9, the inner edge 362 of the left leakage barrier cuff $360_L$ lies above the inner surface of the body fluid absorbent structure 1B and is deformable in vertical and transverse directions as viewed in FIGS. 8 and 9. The inner edge 362 is folded back so as to form a sleeve within which a first elastic member 371 extends in a longitudinal direction of the body fluid absorbent structure 1B and attached in a stretched state thereto. As shown in FIG. 10, the left leakage barrier cuff $360_L$ is folded back in an inverted Z-shape so that the outer edge 361 and the inner edge 362 of this cuff $360_L$ respectively define the bottom and the top of the Z-shape. The left leakage barrier cuff $360_L$ is bonded to itself by means of adhesive 365 while the skin-contactable sheet 4c and the left leakage barrier cuff $360_L$ are bonded to each other also by means of adhesive 365. The first elastic member 371 has its opposite ends fixed to the front and rear ends 331, 332 of the body fluid absorbent structure 1B, respectively, via the leakage barrier cuff $360_L$. The left leakage barrier cuff $360_L$ may include, in addition to the first elastic member 371, second elastic members 372 bonded in a stretched state thereto in a transversely intermediate zone defined between the outer edge 361 and the inner edge 362 and above the inner surface of the body fluid absorbent structure 1B. The second elastic members 372 extend in parallel to the first elastic member 371 between the front and rear ends 363, 364 of the left leakage barrier cuff $360_L$, preferably in the crotch region 6. In the left leakage barrier cuff $360_L$, elastic regions 371a, 372a which are elastically stretchable/contractible in the back-and-forth direction Y are formed along the first elastic member 371 and the second elastic members 372. While the distal ends $23_R$, $23_L$ of the front cross member 21 and the distal ends $24_R$, $24_L$ of the rear cross member 22 may be bonded to the respective inner surfaces of the right leakage barrier cuff $360_R$ and the left leakage barrier cuff $360_L$ to meet the requirements (See FIG. 9), it is preferred to bond these distal ends to the left leakage barrier cuff $360_L$ as the left leakage barrier cuff $360_L$ in the embodiment shown in FIG. 9. Specifically, the distal end $24_L$ is bonded to the left leakage barrier cuff $360_L$ preferably so as to be placed just upon the elastic region 371a or 372a, more preferably so as to be placed just upon the first elastic member 371 or the second elastic members 372 in the elastic region 371a or 372a, respectively. According to the embodiment shown in FIG. 9, the distal end $24_L$ of the rear cross member 22 is attached to the left leakage barrier cuff $360_L$ so as to be placed just upon the second elastic members 372. The first and second elastic members 371, 372 having thitherto been in a state of contraction are stretched as the pants-type diaper 1 is put on the wearer's body and, under a tension of these first and second elastic members 371, 372, the left leakage barrier cuff $360_L$ stands up from the inner surface of the body fluid absorbent structure 1B as indicated by imaginary lines in FIGS. 8 and 9. The front cross member 21 also biases the left leakage barrier cuff $360_L$ to stand up as the front cross member 21 is stretched and prevent the left leakage barrier cuff $360_L$ from collapsing. Just like the case of the leakage barrier barriers in the pants-type diaper of FIG. 1, these leakage barrier cuffs $360_R$, $360_L$ standing up in this manner can be reliably held in close contact around the wearer's legs to prevent body waste from leaking sideways and/or flowing down along the wearer's legs.

Figure 11:
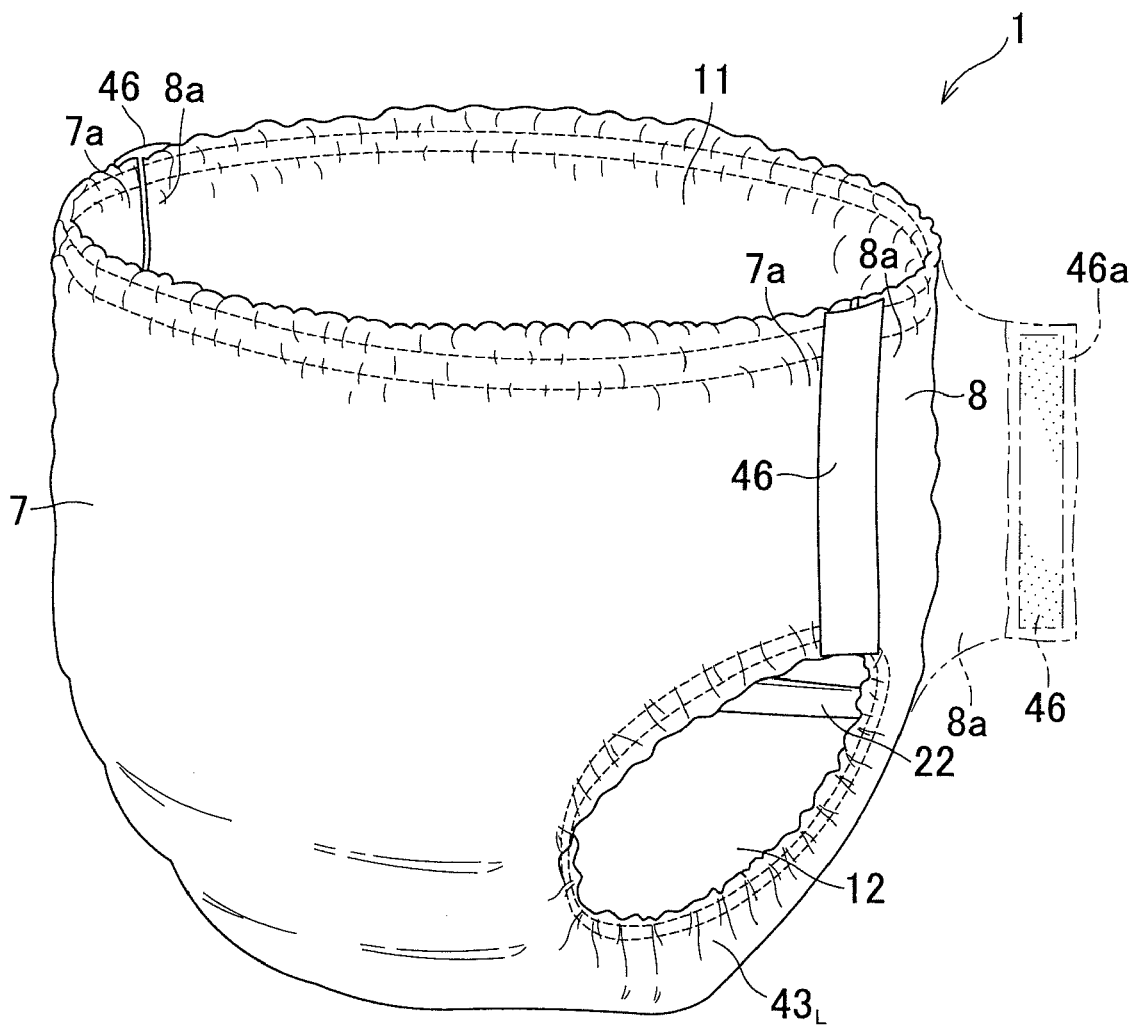
FIG. 11 is a view similar to FIG. 1, showing another preferred embodiment of the invention.

FIG. 11 is a view similar to FIG. 1, showing another preferred embodiment of the invention. The pants-type diaper 1 of FIG. 11 is similar to the pants-type diaper 1 of FIG. 1 except that the rear waist region 8 is provided along the side edges 8a with fasteners 46. These fasteners 46 extend fully along the respective side edges 8a and are adapted to be engaged with the respective outer surfaces of the associated side edges 7a of the front waist region 7 in disengageable and re-engageable manner. To put this pants-type diaper 1 on baby's body, the front and rear waist regions 7, 8 may be previously connected to each other by means of the fasteners 46 to obtain the really pants-like shaped diaper 1. After the waist-opening 11 of this pants-like shaped diaper 1 has been broadened, the procedure to put the pants-type diaper 1 of FIG. 1 on the wearer's body may be followed. After the pants-type diaper 1 has been put on the wearer's body, the fasteners 46 may be peeled off from the front waist region 7 to check existence or nonexistence of body waste and/or to facilitate the pants-type diaper contaminated with body waste to be taken off. The fastener 46 may be selected from the group consisting of a hook member or a loop member of the mechanical fastener well known in the various trade names such as, Velcro and Magic Tape and pressure-sensitive tapes. The respective outer surfaces of the side edges 7a of the front waist region 7 may be defined by materials suitable for cooperation with the fastener 46, for example, nonwoven fabrics or plastic films. It should be noted here that the fastener 46 in the illustrated embodiment is provided along its periphery with a finger-grip 46a.

What is claimed is:

1. A disposable pants-type diaper having a back-and forth direction and a transverse direction, said diaper comprising:
    an inner surface adapted to face a wearer's skin:
    an outer surface adapted to face away the wearer's skin,
    a crotch region;
    a front waist region extending forward in the back-and forth direction from said crotch region;
    a rear waist region extending rearward in the back-and forth direction from said crotch region, wherein said front and rear waist regions are attached to each other along respective lateral edges thereof;
    a body fluid absorbent structure extending below the inner surface;
    leakage barriers extending along side edges of the absorbent structure and including elastic members stretchable in the back-and forth direction in the crotch region; and
    a pair of front and rear belt members, both extending in the transverse direction across said body fluid absorbent structure and bonded to said leakage barriers at end portions of said belt members, respectively;
    wherein
        each of said belt members further includes a middle portion and two intermediate portions extending between said middle portion and said ends portions, respectively, in the transverse direction and being free of direct attachment to the inner surface: and
        said belt members are directly bonded to each other at the middle portions thereof, leaving said intermediate portions free of direct attachment to each other.

2. The pants-type diaper according to claim 1, wherein said respectively distal ends of said belt members are positioned at the same distance from a transverse center line bisecting a dimension of said pants-type diaper as measured along said inner surface in the back-and-forth direction.

3. The pants-type diaper according to claim 1, wherein said belt members are elastically stretchable and contractible and attached to the inner surface at the end portions in a stretched state in the transverse direction.

4. The pants-type diaper according to claim 1, wherein said lateral edges of said front and rear waist regions are respectively detachably attached to each other.

5. The pants-type diaper according to claim 3, further comprising a top sheet defining the inner surface and a back sheet defining the outer surface,
wherein said leakage barriers further comprise
said elastic members positioned between the top and back sheets; and
a pair of flaps of the top and back sheets extending outwardly in the transverse direction from the side edges of said body fluid absorbent structure in said transverse direction, and being riseable up under contraction of said elastic members.

6. The pants-type diaper according to claim 3, wherein said leakage barriers further comprises a pair of leakage barrier cuffs respectively formed along the side edges of said body fluid absorbent structure,
wherein the elastic members are stretchably attached to the leakage barrier cuffs so that the leakage barrier cuffs are riseable up along the side edges of the absorbent structure to prevent leakage of body fluid.

7. The pants-type diaper according to claim 6, wherein said leakage barrier cuffs are directly bonded to said belt members, respectively.

8. The pants-type diaper according to claim 1, wherein both said front and rear belt members extend in the transverse direction over the body fluid absorbent structure.

9. The pants-type diaper according to claim 1, wherein said front and rear belt members connected at the middle portions define two front and rear openings,
the front opening is surrounded by the two intermediate portions of the front belt member and the front waist region,
the rear opening is surrounded by the two intermediate portions of the rear belt member and the rear waist region, and
said two front and rear openings are adapted to guide body fluid passing through.

10. The pants-type diaper according to claim 9, wherein said intermediate portions of the front belt member and the respective intermediate portions of the rear belt member define left and right openings adapted to surround the wearer's legs.

11. The pants-type diaper according to claim 5, wherein said flaps are drawn inwardly of the diaper by said belt members to form the leakage barriers.

12. The pants-type diaper according to claim 1, wherein said leakage barriers further comprises a pair of leakage barrier cuffs respectively formed along the side edges of said body fluid absorbent structure,
the elastic members are stretchably attached to the leakage barrier cuffs so that the leakage barrier cuffs are riseable up along the side edges of the absorbent structure to prevent leakage of body fluid, and
each of said leakage barrier cuffs is fold back in the transverse direction to define an inverted Z-shape further comprising:
an inner portion lying above the body fluid absorbent structure;
an outer portion attaching to the outer surface of the body fluid absorbent structure.

13. The pants-type diaper according to claim 12, wherein said elastic members are bonded to the inner portion of each of the leakage barrier cuffs in a stretched state to form respective elastic regions of the inner portion, and
the end portions of said belt members are bonded to the elastic regions and placed upon the elastic members, thereby, in use, the leakage barrier cuffs stands up from the inner surface on the side edges of the absorbent structure, under tension of the elastic members.

14. The pants-type diaper according to claim 1, wherein said belt members are directly bonded to each other only at the middle portions.

15. The pants-type diaper according to claim 1, further comprising:
a front outer sheet defining said front waist region and a front part of the crotch region;
a rear outer sheet defining said rear waist region and a rear part of the crotch region;
a center sheet defining a third part of the crotch region and attached on said first and second parts of the front and rear sheets to bond the front and rear sheets;
an inner sheet defining the inner surface of the diaper and being disposed over the front sheet, the rear sheet and the center sheet and said body fluid absorbent structure and being intermittently bonded to the inner sheet.

16. The pants-type diaper according to claim 13, wherein the leakage barrier cuffs further comprise other elastic members located at distal edges of each of the leakage barrier cuffs.

* * * * *